US00PP07777P

United States Patent [19]

Holtkamp, Sr.

[11] Patent Number: Plant 7,777

[45] Date of Patent: Jan. 28, 1992

[54] AFRICAN VIOLET PLANT NAMED 'FENJA'

[76] Inventor: Reinhold Holtkamp, Sr.,
Blumenstrasse 28, D 4242
Rees-Haffen, Fed. Rep. of Germany

[21] Appl. No.: 551,444

[22] Filed: Jul. 12, 1990

[51] Int. Cl.[5] ..... A01H 5/00
[52] U.S. Cl. ..... Plt./69
[58] Field of Search ..... Plt./69

[56] References Cited

U.S. PATENT DOCUMENTS

P.P. 6,359 10/1988 Yoshida ..... Plt./68

*Primary Examiner*—James R. Feyrer
*Attorney, Agent, or Firm*—Foley & Lardner

[57] ABSTRACT

A new and distinct cultivar of African violet named Fenja characterized by its single, lilac flowers with darker, purple center radiating into the two small petals; elongated petals; strong, upright flower stems that curve toward the center to form a compact bouquet above the leaves; medium green, oval to round leaves; profuse flowering, vigorous growth habit, flowering 10–11 weeks after potting, and its long-lasting and non-dropping flowers.

1 Drawing Sheet

The present invention comprises a new and distinct cultivar of African violet plant, botanically known as *Saintpaulia ionantha,* and hereafter referred to by the cultivar name Fenja.

The new cultivar was referred to during the breeding and selection process by the designation 906 L.M flie., and is a product of a planned breeding program. The new cultivar was originated from a cross made by me in the controlled breeding program in Haffen, Federal Republic of Germany. The female, or seed parent was a cultivar designated Arizona III. The male, or pollen parent was a cultivar designated 287.

Fenja was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Fenja has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Fenja, which in combination distinguish this African violet as a new and distinct cultivar:

(1) Strong, upright flower stems curving toward the center.
(2) Single lilac flowers with elongated petals and darker center radiating into the two smaller petals.
(3) Profuse flowering.
(4) Each plant carries 10–12 and more upright flower stems, each of which carries 5–7 and more flowers.
(5) Long lasting, non-dropping flowers.
(6) Vigorous grower.
(7) Plant saleable 10 to 11 weeks after potting.

(8) Seed capsules push slightly through.
(9) Medium green, oval to round leaves.
(10) After maturity the flowers dry off and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Color Chart (RHS), except where general colors of ordinary significance are referred to. Color values were taken under natural sunlight conditions at approximately 12 a.m. in Nashville, Tenn.

Botanical classification: *Saintpaulia ionantha,* Ramat., c.v. Fenja.

Parentage:
*Male parent.*—287.
*Female parent.*—Arizona III.

Propagation: The new cultivar holds its distinguishing characteristics through successive propagations by leaf cuttings.

Plant: From 9 cm to 11 cm tall when grown in pots, and approximately 20–25 cm in diameter when fully grown.

*Leaves.*—General form: Oval to round. Diameter: 55–65 mm. Texture: Leatherlike. Aspect: Shiny, hairy. Veins: Upperside: well visible. Underside: very well pronounced, light green, shiny. Color (upperside): Yellow-green group 147 A. Color (underside): Greyed-green group 194 C and Greyed-purple group 186 B to C. Petiole: Very strong, green with purplish-brown touch, hairy.

*Flowers.*—Buds: Bell-shaped, 6–8 mm just before opening, purple. Sepals: Five (5). Color: Brownish-green. Calyx: Shape: Funnel-shaped. Aspect: Spear-shaped, hairy. Peduncle: Character: Strong upright, hairy. Color: Purplish-brown.

*Individual flowers.*—Size: 33–38 mm. Shape: Single with elongated petals and striking size difference between the 3 large and the two small petals. Color (upperside): Large petals are violet group 87 D and lighter. Small petals are Purple-violet vroup 80 C to B. Under cooler temperatures and more intensive lighting, the lilac color tends to intensify. Color (underside): Purple-violet group 80 C to D and lighter. Borne: Each flower stem carries 5–7 and more flowers on strong, upright peduncle that are free standing above the leaves, thereby forming a compact bouquet. Flowering Habit: Flowers 10–11 weeks after potting.

*Reproductive organs.*—Stamens: Two (2). Anthers: 2 composed of 4 anther cells, seed capsule pushes slightly through. Filaments: Yellowish white, 3–4 mm long. Pollen Color: Yellow Group 7 A. Styles: 6 mm long, purple, base of ovary light green and hairy.

*Roots.*—Normally developed, white when young, turning slightly brownish when older.

Disease resistance: Good.

General observations:

Fenja has a very attractive appearances due to its lilac flowers with darker, purple center radiating into the two small petals. A tight bouquet of flowers free standing above the leaves develops after approximately 10–11 weeks. Each of the 10–12 and more flower stems carries 5–7 single flowers with elongated petals. The size difference between the 3 large and the two small petals is striking. The flowers are long-lasting and non-dropping and the seed capsules push slightly through. Medium green, oval to round leaves give the plant a fresh look.

I claim:

1. A new and distinct cultivar of African violet named Fenja, as described and illusrated, and particularly characterized by its single, lilac flowers with darker, purple center radiating into the two small petals; elongated petals; strong, upright flower stems that curve toward the center to form a compact bouquet above the leaves; medium green, oval to round leaves; profuse flowering, vigorous growth habit, flowering 10–11 weeks after potting, and its long-lasting and non-dropping flowers.

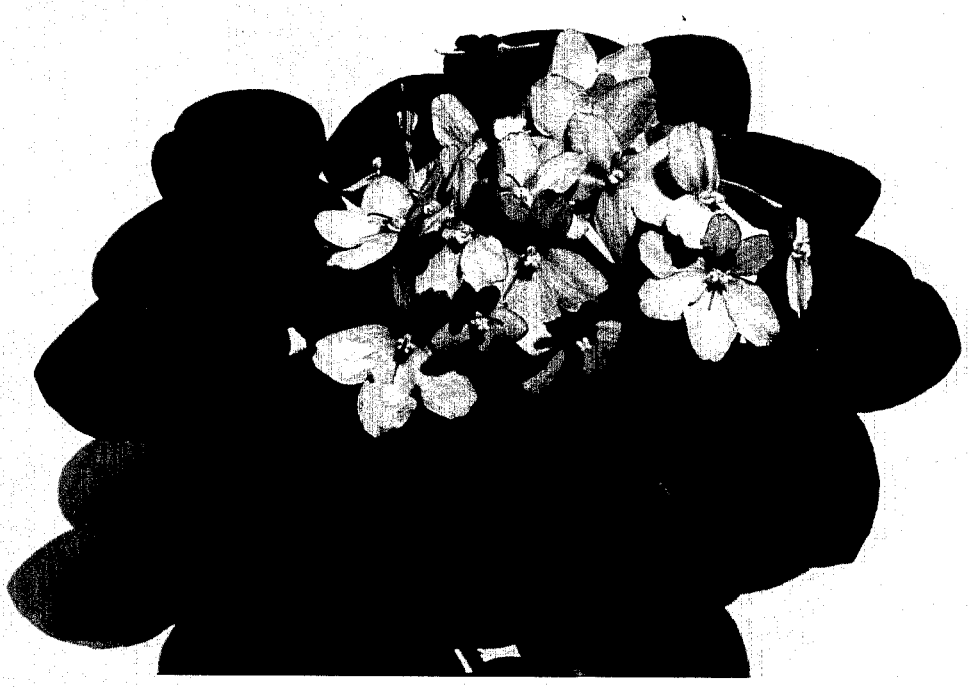

* * * * *